(12) United States Patent
Tsuda

(10) Patent No.: US 8,982,198 B2
(45) Date of Patent: Mar. 17, 2015

(54) IMAGE SIGNAL CORRECTION APPARATUS, IMAGING APPARATUS, ENDOSCOPIC APPARATUS

(75) Inventor: Takashi Tsuda, Oume (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 381 days.

(21) Appl. No.: 13/473,321

(22) Filed: May 16, 2012

(65) Prior Publication Data

US 2013/0100263 A1  Apr. 25, 2013

(30) Foreign Application Priority Data

Oct. 21, 2011 (JP) ................................. 2011-232254

(51) Int. Cl.
| | | |
|---|---|---|
| A62B 1/04 | (2006.01) | |
| H04N 5/213 | (2006.01) | |
| A61B 1/00 | (2006.01) | |
| G06T 5/00 | (2006.01) | |
| G06T 5/50 | (2006.01) | |
| H04N 5/21 | (2006.01) | |

(52) U.S. Cl.
CPC .................. *H04N 5/213* (2013.01); *H04N 5/21* (2013.01); *A61B 1/00009* (2013.01); *A61B 1/00186* (2013.01); *G06T 5/002* (2013.01); *G06T 5/50* (2013.01); *G06T 2207/10068* (2013.01); *G06T 2207/20148* (2013.01); *G06T 2207/20224* (2013.01)
USPC .................... 348/65; 348/61; 348/62; 348/63; 348/64; 348/66

(58) Field of Classification Search
CPC . G06T 5/002; G06T 5/50; G06T 2207/10068; G06T 2207/20148; G06T 2207/20224; H04N 5/213; H04N 5/21; H04N 2005/2255; H04N 7/183; A61B 1/00009; A61B 1/00186; A61B 1/05; A61B 1/042; A61B 1/045

USPC .......................................................... 348/65
See application file for complete search history.

(56) References Cited

U.S. PATENT DOCUMENTS

| | | | | |
|---|---|---|---|---|
| 5,532,765 | A * | 7/1996 | Inoue et al. | 348/807 |
| 7,095,787 | B2 * | 8/2006 | Kadono et al. | 375/240.27 |
| 7,777,762 | B2 * | 8/2010 | Katano et al. | 345/632 |
| 8,041,109 | B2 * | 10/2011 | Higashimoto | 382/167 |
| 2002/0026093 | A1 * | 2/2002 | Ooyatsu | 600/118 |
| 2005/0232483 | A1 * | 10/2005 | Kato et al. | 382/171 |
| 2007/0102623 | A1 * | 5/2007 | Fengler et al. | 250/208.1 |
| 2008/0317454 | A1 * | 12/2008 | Onuki | 396/128 |
| 2009/0086174 | A1 * | 4/2009 | Fukumoto et al. | 355/29 |
| 2009/0317016 | A1 | 12/2009 | Cho et al. | |
| 2011/0273548 | A1 * | 11/2011 | Uchiyama et al. | 348/68 |
| 2011/0292258 | A1 * | 12/2011 | Adler et al. | 348/263 |
| 2012/0127292 | A1 * | 5/2012 | Yamazaki | 348/68 |

FOREIGN PATENT DOCUMENTS

| | | |
|---|---|---|
| JP | 2009-027608 | 5/2009 |
| JP | 2009-232402 | 10/2009 |
| JP | 2010-004266 | 1/2010 |

\* cited by examiner

*Primary Examiner* — Andy Rao
*Assistant Examiner* — Shan Elahi
(74) *Attorney, Agent, or Firm* — Blakely, Sokoloff, Taylor & Zafman LLP

(57) ABSTRACT

An image signal correction apparatus includes: a frame memory configured to hold input image signals corresponding to a predetermined number of frames; a difference calculation unit configured to calculate a difference signal between an input image signal and each of the image signals held in the frame memory; a filter unit configured to pass a difference signal having a value equal to or smaller than a threshold value; and a control unit configured to change the threshold value of the filter unit in accordance with the value of the difference signal calculated in the difference calculation unit.

10 Claims, 10 Drawing Sheets

IMAGE SIGNAL CORRECTION APPARATUS, IMAGING APPARATUS, ENDOSCOPIC APPARATUS

CROSS-REFERENCE TO RELATED APPLICATION

This application is based upon and claims the benefit of priority from the prior Japanese Patent Application No. 2011-232254, filed on Oct. 21, 2011; the entire contents of which are incorporated herein by reference.

FIELD

An embodiment described herein relates generally to an image signal correction apparatus, an imaging apparatus and an endoscopic apparatus.

BACKGROUND

To reduce a physical burden on patients, a surgery using an imaging apparatus, e.g., an endoscopic apparatus, has conventionally been performed. In the endoscopic apparatus, a scope is inserted into a body of a patient, and an image is captured while an affected part is being illuminated. However, depending on a light source that illuminates the affected part or a condition of the affected part, an image having a very low contrast is obtained. Therefore, in a conventional endoscopic apparatus, image processing in which an outline is emphasized to provide a contrast is performed. Further, other than a contrast, noise caused in an image also hinders the condition of the affected part from being recognized. In this regard, various methods of reducing noise have conventionally been proposed.

DETAILED DESCRIPTION

An image signal correction apparatus according to an embodiment including: a frame memory configured to hold input image signals corresponding to a predetermined number of frames; a difference calculation unit configured to calculate a difference signal between an input image signal and each of the image signals held in the frame memory; a filter unit configured to pass a difference signal having a value equal to or smaller than a threshold value; and a control unit configured to change the threshold value of the filter unit in accordance with the value of the difference signal calculated in the difference calculation unit.

Hereinafter, an embodiment will be described with reference to the drawings.

Embodiment

Figure 1:
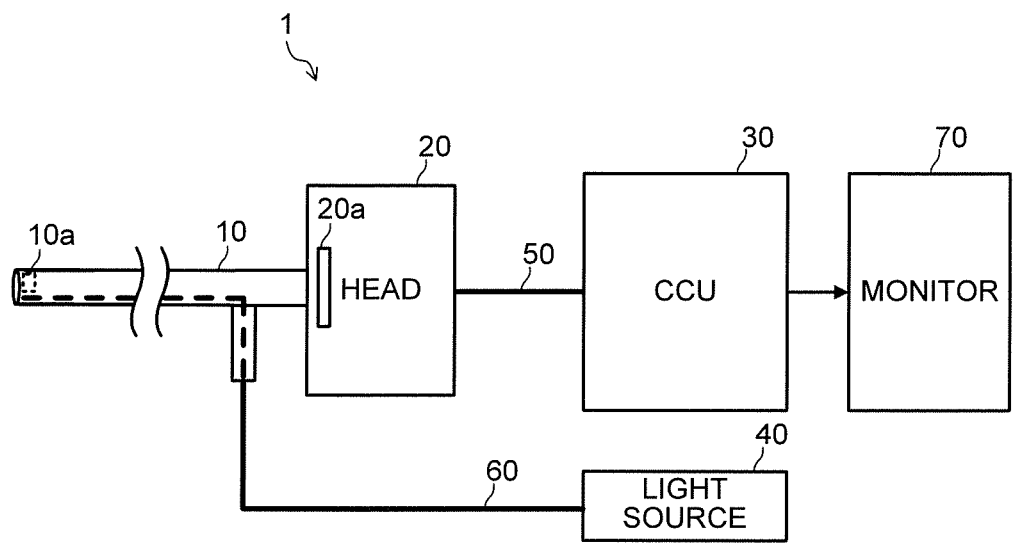
FIG. 1 is a structural diagram of an endoscopic apparatus according to an embodiment.

In this embodiment, a structure of a rigid endoscopic apparatus will be explained as an example of an imaging apparatus. FIG. 1 is a structural diagram of an endoscopic apparatus 1 according to the embodiment (hereinafter, referred to as endoscopic apparatus 1). In this embodiment, an embodiment in which a CMOS (Complementary Metal Oxide Semiconductor) image sensor is adopted as an imaging device will be described, but a CCD (Charge Coupled Device) image sensor may also be adopted as an imaging device.

The endoscopic apparatus 1 includes a scope 10, a head 20, a CCU (Camera Control Unit) 30, a light source 40, an optical fiber 60, and a monitor 70. The scope 10 includes an objective lens 10a at a tip thereof and is inserted into a subject to be inspected. The head 20 outputs RGB image signals (hereinafter, referred to simply as image signal) to the CCU 30 via a camera cable 50, the RGB image signals being captured by a CMOS image sensor 20a (hereinafter, referred to simply as image sensor 20a) located on an imaging surface of the objective lens 10a. The CCU 30 processes the image signal output from the head 20. The light source 40 illuminates an imaging range. The optical fiber 60 is for introducing light emitted from the light source 40 into a tip end of the scope 10. The monitor 70 displays an image corresponding to the captured image signal.

The camera cable 50 houses a signal line for transmitting and receiving the image signal and a control signal between the head 20 and the CCU 30, a power line for supplying power from the CCU 30 to the head 20, and the like.

Figure 2:
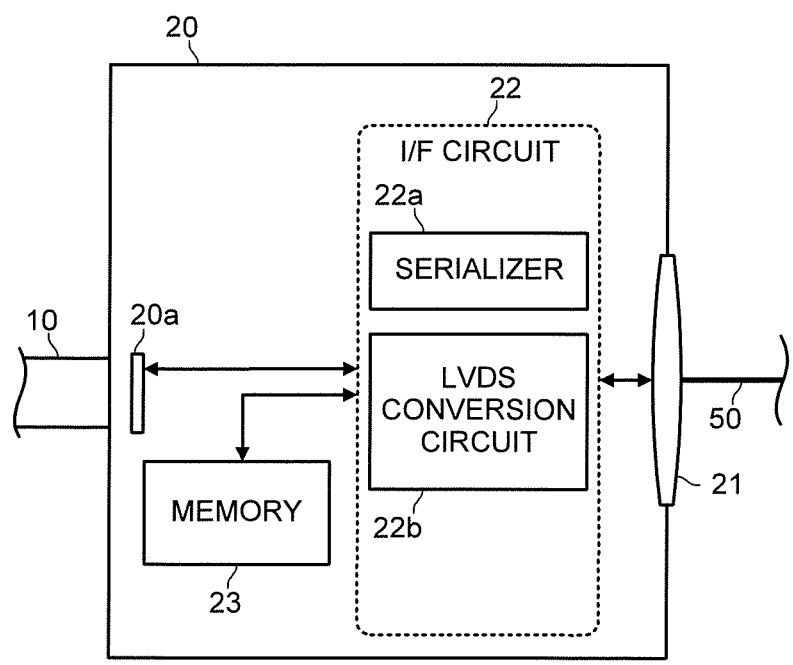
FIG. 2 is a structural diagram of a head of the endoscopic apparatus according to the embodiment.

FIG. 2 is a structural diagram of the head 20. The head 20 includes the image sensor 20a, a connection terminal 21, an I/F circuit 22, and a memory 23. The image sensor 20a is a digital-color CMOS image sensor corresponding to a full high definition and is constituted of three 1/3-type CMOS sensors. In this embodiment, it is assumed that the image sensor 20a is driven by progressive scanning, but it may be driven by interlaced scanning.

To the connection terminal 21, the camera cable 50 is connected. The I/F circuit 22 is an LVDS (Low Voltage Differential Signaling) serializer and includes a serializer 22a and an LVDS conversion circuit 22b. The I/F circuit 22 transmits an image signal output from the image sensor 20a as it is as a digital signal to the CCU 30 via the camera cable 50 connected to the connection terminal 21. At that time, image signals of R (red), G (green), and B (blue) (specifically, data of concentration values (gradation) of pixels constituting screen) are transferred through signal lines that are independent from one another. Therefore, a high-quality image can be displayed as compared to a conventional analog transmission of RGB signals. The memory 23 is, for example, a flash memory and stores setting conditions of the image sensor 20a (for example, frame rate, gain, etc.).

Figure 3:
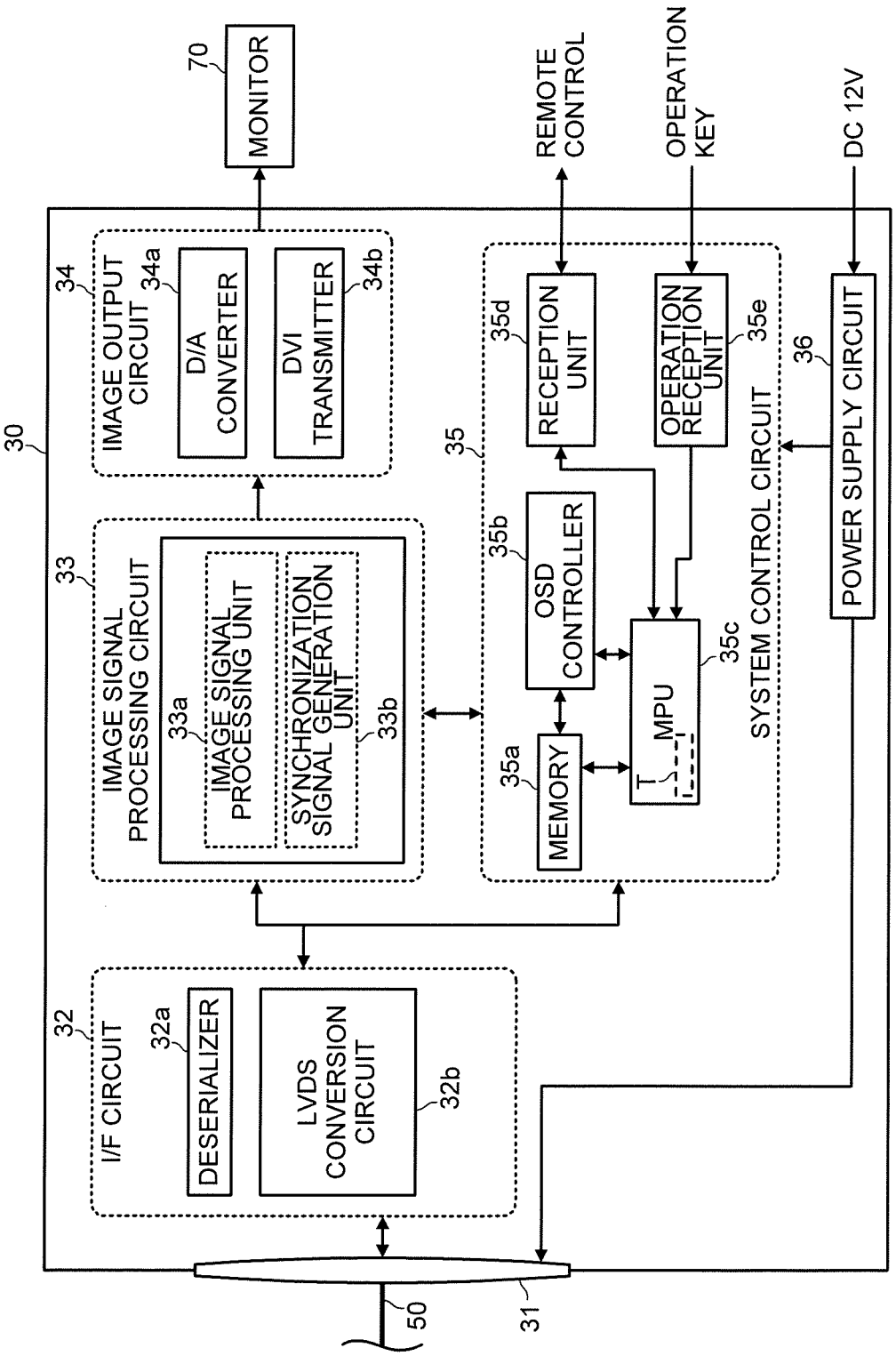
FIG. 3 is a structural diagram of a CCU of the endoscopic apparatus according to the embodiment.

FIG. 3 is a structural diagram of the CCU 30. The CCU 30 includes a connection terminal 31, an I/F circuit 32, an image signal processing circuit 33, an image output circuit 34, a system control circuit 35, and a power supply unit 36. To the connection terminal 31, the camera cable 50 is connected.

The I/F circuit 32 is an LVDS deserializer and includes a deserializer 32a and an LVDS conversion circuit 32b. The I/F circuit 32 outputs the image signal transmitted from the head 20 to the image signal processing circuit 33. The I/F circuit 32 transmits a control signal output from the system control circuit 35 to the head 20 via the camera cable 50 connected to the connection terminal 31.

The image signal processing circuit 33 includes an image signal processing unit 33a and a synchronization signal generation unit 33b. The image signal processing unit 33a processes the image signal output from the I/F circuit 32 and outputs the processed image signal to the image output circuit 34. Specifically, the image signal processing unit 33a performs processing of suppressing noise that is caused in an area of movement in the image signal. It should be noted that details of the image signal processing unit 33a will be described with reference to FIG. 5 to FIG. 7.

The synchronization signal generation unit 33b generates a synchronization signal used for imaging by the image sensor 20a. The synchronization signal is generated at predetermined intervals that correspond to a set frame rate (for example, 1/30 seconds, 1/60 seconds, and the like). The generated synchronization signal is output to an MPU (Micro Processing Unit) 35c and transmitted from the I/F circuit 32 to the head 20 via the camera cable 50 connected to the connection terminal 31.

The image output circuit 34 includes a D/A converter 34a and a DVI (Digital Visual Interface) transmitter 34b. The image output circuit 34 outputs the image signal processed in the image signal processing circuit 33 to the monitor 70 as analog and/or digital RGB image signals.

The system control circuit 35 includes a memory 35a, an OSD (On-screen Display) controller 35b, the MPU 35c, a reception unit 35d, and an operation reception unit 35e. The system control circuit 35 controls the endoscopic apparatus 1.

The memory 35a is, for example, an EEPROM (Electrically Erasable Programmable Read-Only Memory) or a flash memory. The memory 35a stores a program for operating the MPU 35c.

The MPU 35c controls the head 20, the CCU 30, and the light source 40 on the basis of a remote control signal received in the reception unit 35d, processed information received in the operation reception unit 35e, and setting information stored in the memory 35a. The MPU 35c incorporates a timer T for counting a time (hereinafter, referred to as built-in timer T).

The OSD controller 35b superimposes text data, a bit-mapped image, and the like on an image of the image signal that is processed in the image signal processing unit 33a and displays the resultant image.

The reception unit 35d receives a control signal for remote control, which is transmitted from an external PC or the like, and outputs the control signal to the MPU 35c. Communication with the external PC is carried out via an RS232-C serial port. The operation reception unit 35e receives processing operated with use of an external operation key and outputs a processing instruction to the MPU 35c.

The power supply unit 36 converts externally-supplied power into a predetermined voltage and supplies the power to the units of the CCU 30. Further, the power described above is also supplied to the head 20 via the camera cable 50 connected to the connection terminal 31.

Figure 4:
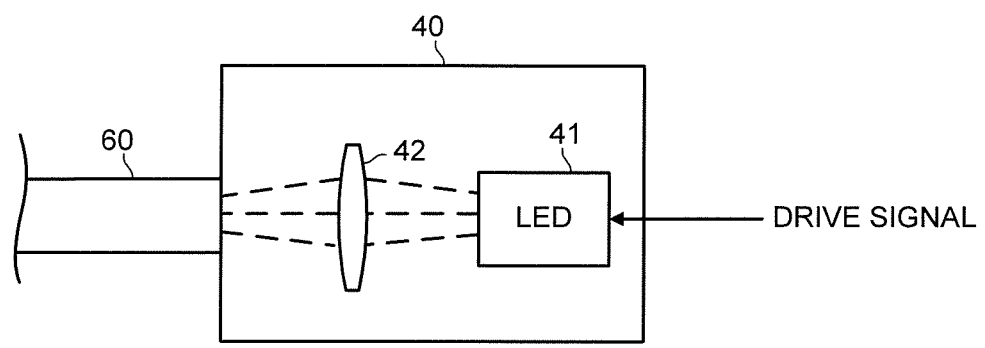
FIG. 4 is a structural diagram of a light source of the endoscopic apparatus according to the embodiment.

FIG. 4 is a structural diagram of the light source 40. The light source 40 includes an LED (Light Emitting Diode) 41 and a lens 42. Further, to the light source 40, the optical fiber 60 is connected. The LED 41 illuminates an imaging range of the image sensor 20a. The lens 42 introduces light emitted from the LED 41 into the optical fiber 60. The light introduced into the optical fiber 60 is guided to the tip end of the scope 10 to illuminate the imaging range of the image sensor 20a, that is, an affected part.

Figure 5:
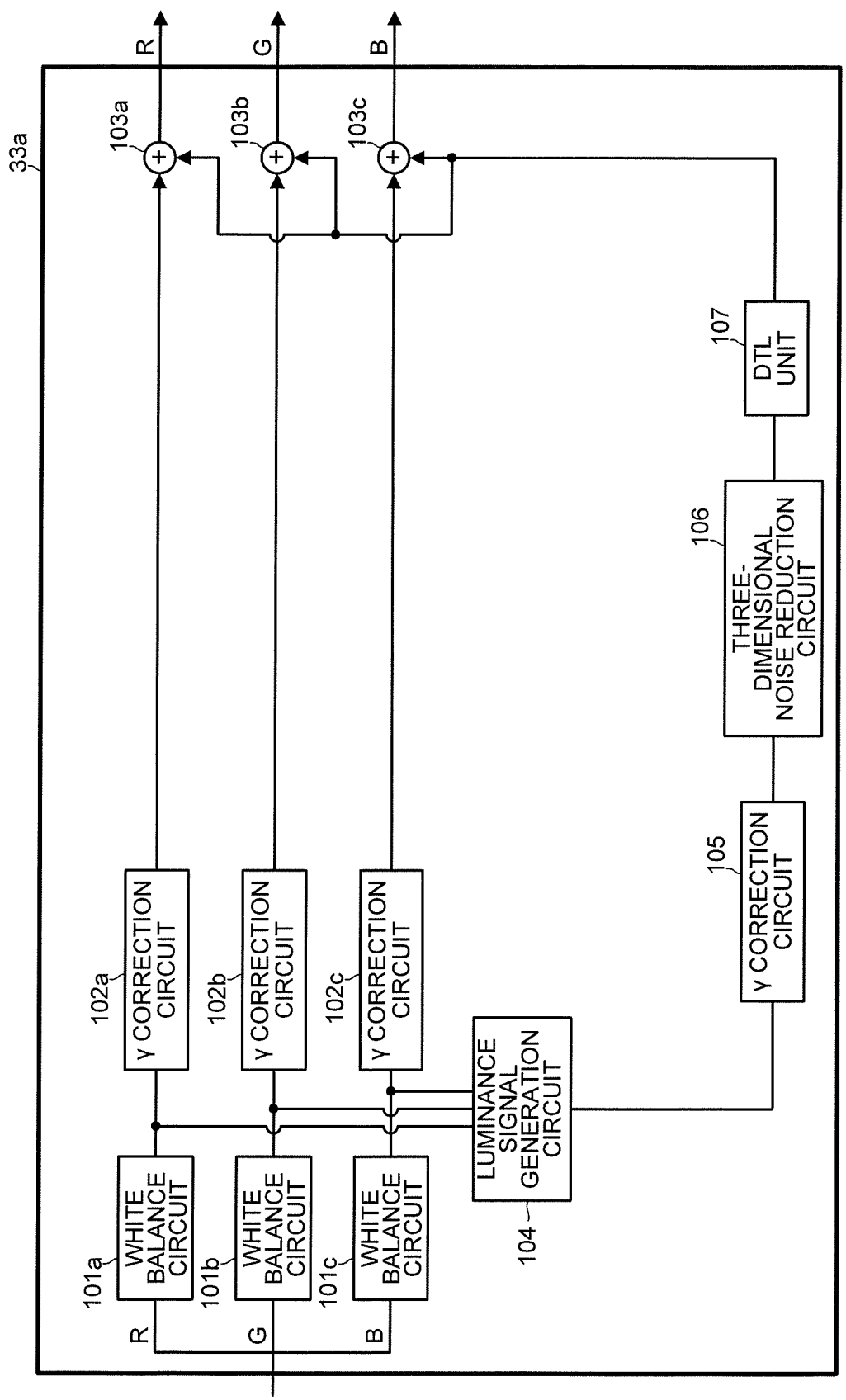
FIG. 5 is a structural diagram of an image signal processing unit of the endoscopic apparatus according to the embodiment.

FIG. 5 is a structural diagram of the image signal processing unit 33a. The image signal processing unit 33a includes white balance circuits 101a to 101c, γ correction circuits 102a to 102c, adders 103a to 103c, a luminance signal generation circuit 104, a γ correction circuit 105, a three-dimensional noise reduction circuit 106, and a DTL unit 107.

In this embodiment, the image signal processing unit 33a is constituted of an FPGA (Field-Programmable Gate Array), but it may be realized by another structure. For example, a function provided to the image signal processing unit 33a may be realized by software (program).

The image signal processing unit 33a suppresses noise caused in an area of movement in the image signal. Hereinafter, a specific structure of the image signal processing unit 33a will be described. It should be noted that a mechanism in which noise is caused in an area of movement will first be described.

Figure 6A:
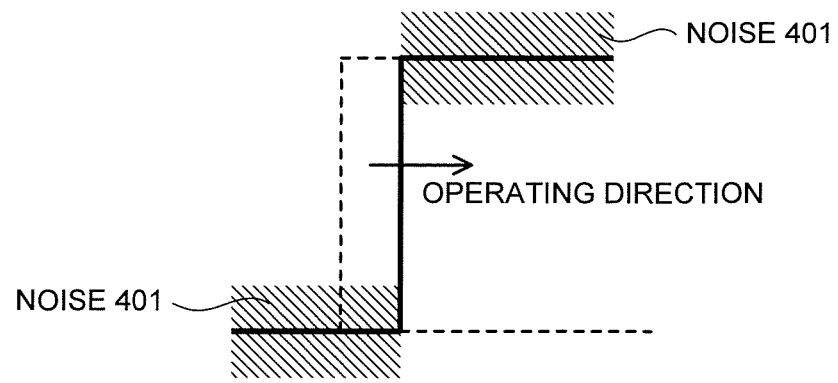
FIG. 6A, FIG. 6B, and FIG. 6C are explanatory diagrams of a noise generation mechanism.
Figure 6B:
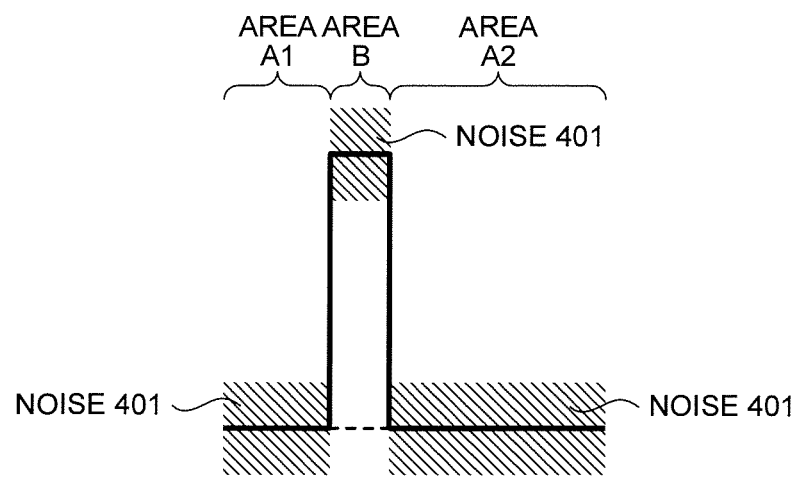
Figure 6C:
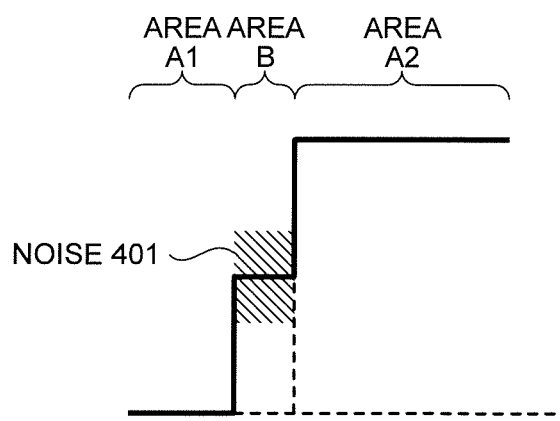

FIG. 6A, FIG. 6B, and FIG. 6C are explanatory diagrams of a noise generation mechanism. FIG. 6A shows a state where a subject (target to be imaged) moves from left to right between continuous frames. A broken line in FIG. 6A indicates a position of the subject in an n-th frame (first frame). A solid line in FIG. 6A indicates a position of the subject in an (n+1)-th frame (second frame) that is one frame after the n-th frame. Shaded portions in FIG. 6A indicate noise 401.

FIG. 6B shows a difference between the first frame and the second frame. Areas A1 and A2 are each an area in which the difference between the first frame and the second frame is zero (hereinafter, referred to as still image area A). In other words, the areas A1 and A2 are areas in which an effect of a three-dimensional noise reduction, that is, an effect of reducing the noise 401 caused at random in terms of time is obtained. An area B is an area in which the difference between the first frame and the second frame exists (hereinafter, referred to as moving image area B). The area B is an area in which an effect of a three-dimensional noise reduction is not obtained.

FIG. 6C is a diagram showing a state where the difference between the first frame and the second frame is mixed into the second frame. In FIG. 6C, a mixing ratio of the difference is set to be 50%. As shown in FIG. 6C, in the still image areas A1 and A2, an image change due to noise is averaged in terms of time so that the noise 401 is reduced. On the other hand, in the moving image area B, the noise 401 is not reduced and left in a visually-recognizable state. The image signal processing unit 33a reduces this noise shown in FIG. 6C by correction.

Hereinafter, with reference to FIG. 5, the structure of the image signal processing unit 33a will be described. The white balance circuits 101a to 101c adjust white balance of an image signal for each of R, G, and B channels. The γ correction circuits 102a to 102c correct the image signals, the white balance of which have been adjusted, for the R, G, and B channels in accordance with characteristics of the monitor 70 such that brightness and a color of the image are correctly displayed on the monitor 70.

The luminance signal generation circuit 104 generates a luminance signal Y for each pixel constituting the screen, based on the image signals of the R, G, and B channels, the white balance of which have been adjusted. To calculate the luminance signal Y, the following expression (1) is used. It should be noted that each of symbols "a", "b", and "c" represents an optional coefficient.

$$Y=aR+bG+cB \quad (1)$$

(a+b+c=1)

The γ correction circuit 105 corrects the luminance signal Y generated in the luminance signal generation circuit 104 in accordance with the characteristics of the monitor 70.

Figure 7:
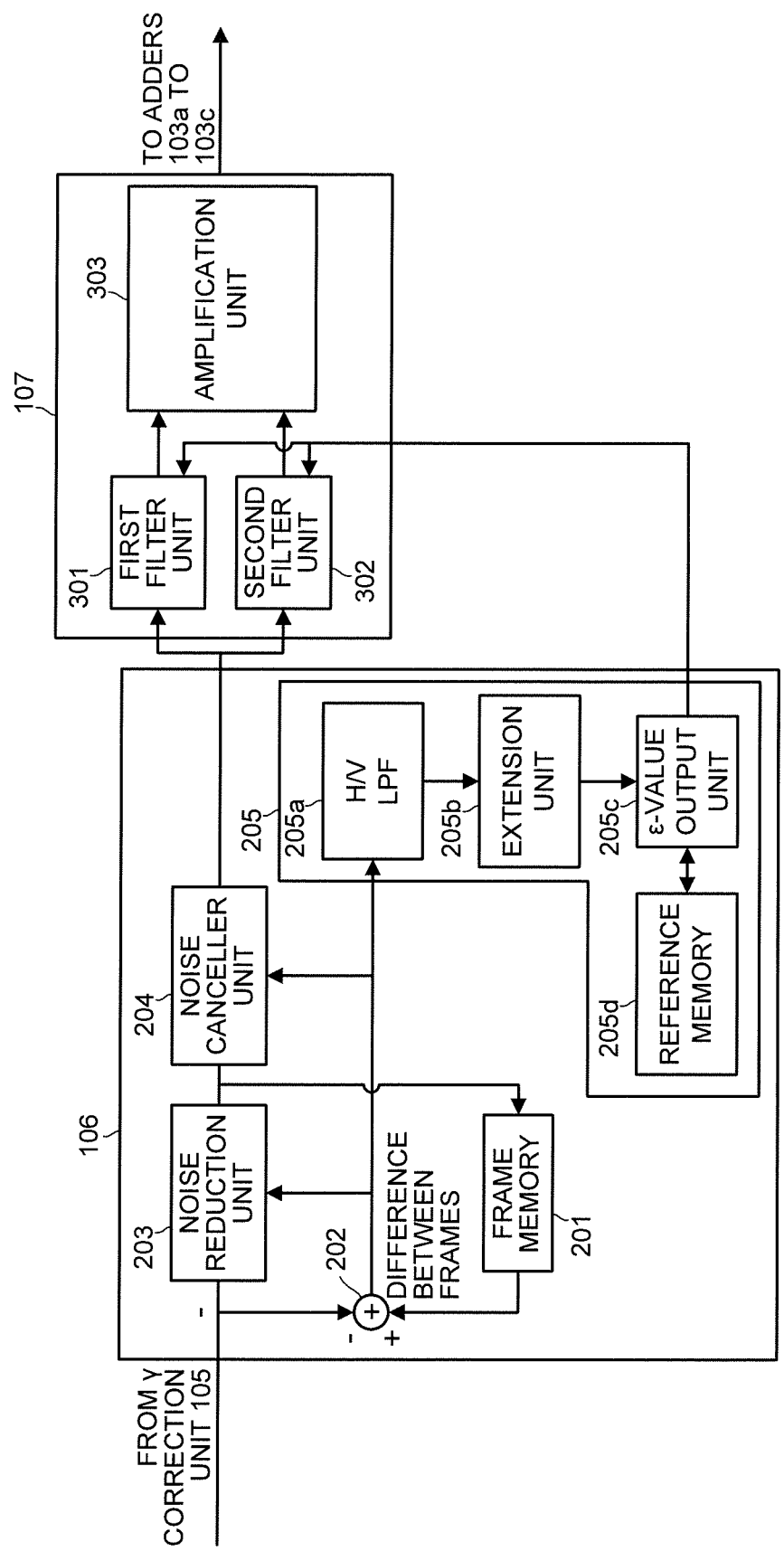
FIG. 7 is a structural diagram of a three-dimensional noise reduction circuit and a DTL unit of the endoscopic apparatus according to the embodiment.

FIG. 7 is a structural diagram of the three-dimensional noise reduction circuit 106 and the DTL unit 107. The three-dimensional noise reduction circuit 106 includes a frame memory 201, an adder 202, a noise reduction unit (for still image) 203, a noise canceller unit (for moving image) 204, and a DTL control unit 205.

The frame memory 201 holds data of a luminance signal from which noise in a still image portion has been reduced by the noise reduction unit 203, in an amount corresponding to a predetermined number of frames.

The adder 202 calculates a difference signal between the luminance signal that is input from the γ correction circuit 105 and the luminance signal that is held in the frame memory 201 (hereinafter, referred to simply as difference signal).

The noise reduction unit 203 has a function of reducing noise of a still image and performs correction to suppress a residual image caused in the image signal. The noise reduction unit 203 calculates an absolute value of the difference signal that is input from the γ correction circuit 105 and performs correction to decrease, in accordance with a magnitude of the absolute value, a mixing ratio with respect to the difference signal output from the γ correction circuit 105. Specifically, as the absolute value becomes larger, that is, as the area has more vigorous movement, the mixing ratio is decreased more to reduce a frame-cyclic amount so that noise in a still image is suppressed.

The noise canceller unit 204 has a function of reducing noise of a moving image and performs correction to suppress degradation of a resolution. The noise canceller unit 204 calculates an absolute value of the difference signal that is input from the γ correction circuit 105 and corrects the difference signal output from the γ correction circuit 105 in accordance with a magnitude of the absolute value.

Specifically, as the absolute value becomes smaller, that is, as the area has less movement, the mixing ratio of the difference signal that has passed through an LPF (Low-Pass Filter) is decreased more so that noise caused in a moving image is suppressed.

The DTL control unit 205 includes an H/V LPF (H/V Low-Pass Filter) 205a, an extension unit 205b, an ε-value output unit 205c, and a reference memory 205d. The H/V LPF 205a is a filter unit having a function of passing a lower frequency component than a predetermined threshold value out of signal components of the difference signal in a horizontal direction and a vertical direction. By passing the difference signal through the H/V LPF 205a, a noise component of the difference signal is removed.

To interpolate information of an edge portion of the difference signal that is lost by the H/V LPF 205a, the extension unit 205b obtains an absolute value of the difference signal from which the noise component has been removed and then calculates, for example, maximum values in every three pixels per line in the horizontal direction and the vertical direction to thereby perform processing of extending the edge portion of the difference signal.

The ε-value output unit 205c refers to the reference memory 205d and outputs to the DTL unit 107 an ε value corresponding to an absolute value V of the difference signal that is output from the extension unit 205b (hereinafter, referred to simply as absolute value V).

Figure 8:
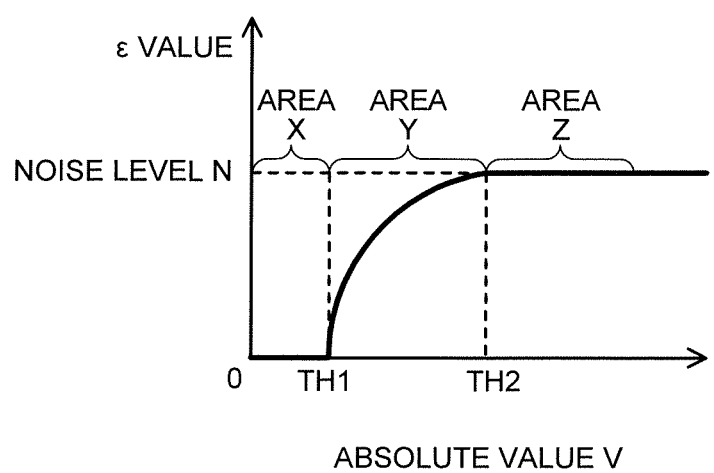
FIG. 8 is a diagram of correction data stored in a memory of the endoscopic apparatus according to the embodiment.

FIG. 8 shows correction data that is stored in the reference memory 205d. The horizontal axis in FIG. 8 indicates an absolute value V output from the extension unit 205b. The vertical axis in FIG. 8 indicates an ε value output to the DTL unit 107. As shown in FIG. 8, in this embodiment, the absolute value V of the difference signal that is output from the extension unit 205b is divided into three areas X, Y, and Z on the basis of comparison with a threshold value TH1 and a threshold value TH2.

(Area X)

The area X is an area in which the absolute value V output from the extension unit 205b is smaller than the threshold value TH1. In the case where the absolute value V output from the extension unit 205b falls within this area X, the image signal is considered to correspond to a still image, and an ε value to be output to the DTL unit 107 is set to zero.

(Area Y)

The area Y is an area in which the absolute value V output from the extension unit 205b is the threshold value TH1 or more and smaller than the threshold value TH2. In the case where the absolute value V output from the extension unit 205b falls within this area Y, the image signal is considered to be in a state where a still image and a moving image are mixed, and an ε value to be output to the DTL unit 107 is changed in accordance with the absolute value V.

In this embodiment, a relationship between the absolute value V output from the extension unit 205b and the ε value output to the DTL unit 107 is set to be a trigonometric function, specifically, the following expression (2).

$$\epsilon(V)=N\cos\{\pi\times(V-TH2)/(2(TH1-TH2))\} \quad (2)$$

It should be noted that the relationship between the absolute value V output from the extension unit 205b and the ε value output to the DTL unit 107 may be set to be a linear function, specifically, the following expression (3).

$$\epsilon(V)=N/(TH2-TH1)(V-TH1) \quad (3)$$

(Area Z)

The area Z is an area in which the absolute value V output from the extension unit 205b is the threshold value TH2 or more. In the case where the absolute value V output from the extension unit 205b falls within this area Z, the image signal is considered to correspond to a moving image, and an ε value to be output to the DTL unit 107 is set to a noise level N.

Figure 9A:
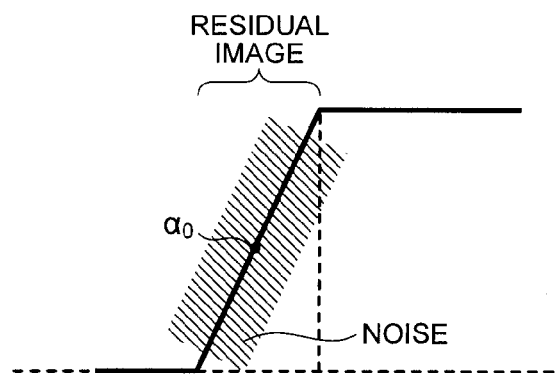
FIG. 9A and FIG. 9B are explanatory diagrams of a noise level.
Figure 9B:
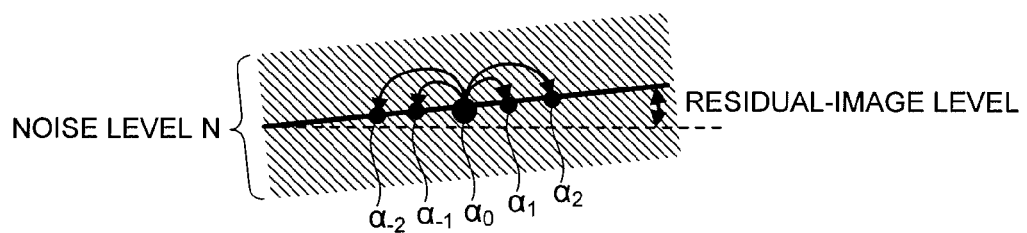

Here, the reason why an ε value to be output to the DTL unit 107 is set to a noise level N in the area Z will be described with reference to FIG. 9A and FIG. 9B. FIG. 9A and FIG. 9B are explanatory diagrams of the noise level N. FIG. 9A shows a state of the area B explained with reference to FIG. 6C. The area B in FIG. 6C is actually in a state where the area A1 and the area A2 are inclined as shown in FIG. 9A. FIG. 9B is an enlarged diagram of a pixel of interest $\alpha_0$ and a circumference thereof in FIG. 9A.

In the area Z, since the ε value is calculated as a difference value between a pixel of interest $\alpha_0$ and a neighboring pixel $\alpha_{-2}$, $\alpha_{-1}$, $\alpha_{+1}$, $\alpha_{+2}$, or the like, the ε value takes a value substantially equal to a difference value between frames. It should be noted that the difference value between the pixel of interest $\alpha_0$ and the neighboring pixel $\alpha_{-2}$, $\alpha_{-1}$, $\alpha_{+1}$, $\alpha_{+2}$, or the like includes a residual-image level and a noise level N as shown in FIG. 9B. However, the difference in the residual-image level N between the pixel of interest $\alpha_0$ and the neighboring pixel $\alpha_{-2}$, $\alpha_{-1}$, $\alpha_{+1}$, $\alpha_{+2}$, or the like takes an extremely smaller value than the difference in the noise level N therebetween. Therefore, the difference in the residual-image level N can be ignored practically, and the difference value between the pixel of interest $\alpha_0$ and the neighboring pixel $\alpha_{-2}$, $\alpha_{-1}$, $\alpha_{+1}$, $\alpha_{+2}$, or the like becomes substantially a value of the noise level N.

Therefore, when the $\epsilon$ value is set to be larger than the value of the noise level N, there is a fear that excessive correction not only to remove noise in the moving image area but also to correct even an image signal may be performed with high probability. In this embodiment, a maximum value of the $\epsilon$ value is set to a noise level N so that excessive correction is prevented from being performed.

The noise level N is calculated in advance as follows. A threshold value is set for a difference signal to count how many pixels whose difference signals exceed the threshold value there are in one frame (one screen). Next, the threshold value is changed so that the threshold value at which the number of pixels each having a difference signal value exceeding the threshold value is about 0.5% of the total number of pixels in one frame, for example, is set to the noise level N.

As shown in FIG. 7, the DTL unit 107 includes a first filter unit 301, a second filter unit 302, and an amplification unit 303. The first filter unit 301 is an $\epsilon$ filter. Specifically, the first filter unit 301 calculates a difference between a value of a pixel to be processed (target pixel) and a value of a neighboring pixel located in a horizontal direction of the target pixel. The first filter unit 301 assumes, as a signal, a pixel in which the difference is larger than the $\epsilon$ value output from the $\epsilon$-value output unit 205c, and does not perform filtering processing. However, the first filter unit 301 assumes, as noise, a pixel in which the difference between the pixel value of the neighboring pixel and that of the target pixel is equal to or smaller than the $\epsilon$ value that is output from the $\epsilon$-value output unit 205c, and performs LPF (Low-Pass Filter) processing in the horizontal direction.

The second filter unit 302 is an E filter. The second filter unit 302 calculates a difference between a value of a pixel to be processed (target pixel) and a value of a neighboring pixel located in a vertical direction of the target pixel. The second filter unit 302 assumes, as a signal, a pixel in which the difference is larger than the value output from the $\epsilon$-value output unit 205c, and does not perform filtering processing. However, the second filter unit 302 assumes, as noise, a pixel in which the difference between the pixel value of the neighboring pixel and that of the target pixel is equal to or smaller than the $\epsilon$ value that is output from the $\epsilon$-value output unit 205c, and performs LPF (Low-Pass Filter) processing in the vertical direction.

The amplification unit 303 amplifies the signals that are output from the first filter unit 301 and the second filter unit 302.

The adders 103a to 103c add the signals output from the DTL unit 107 to the image signals in the respective R, G, and B channels.

(Operation of Endoscopic Apparatus 1)

Figure 10:
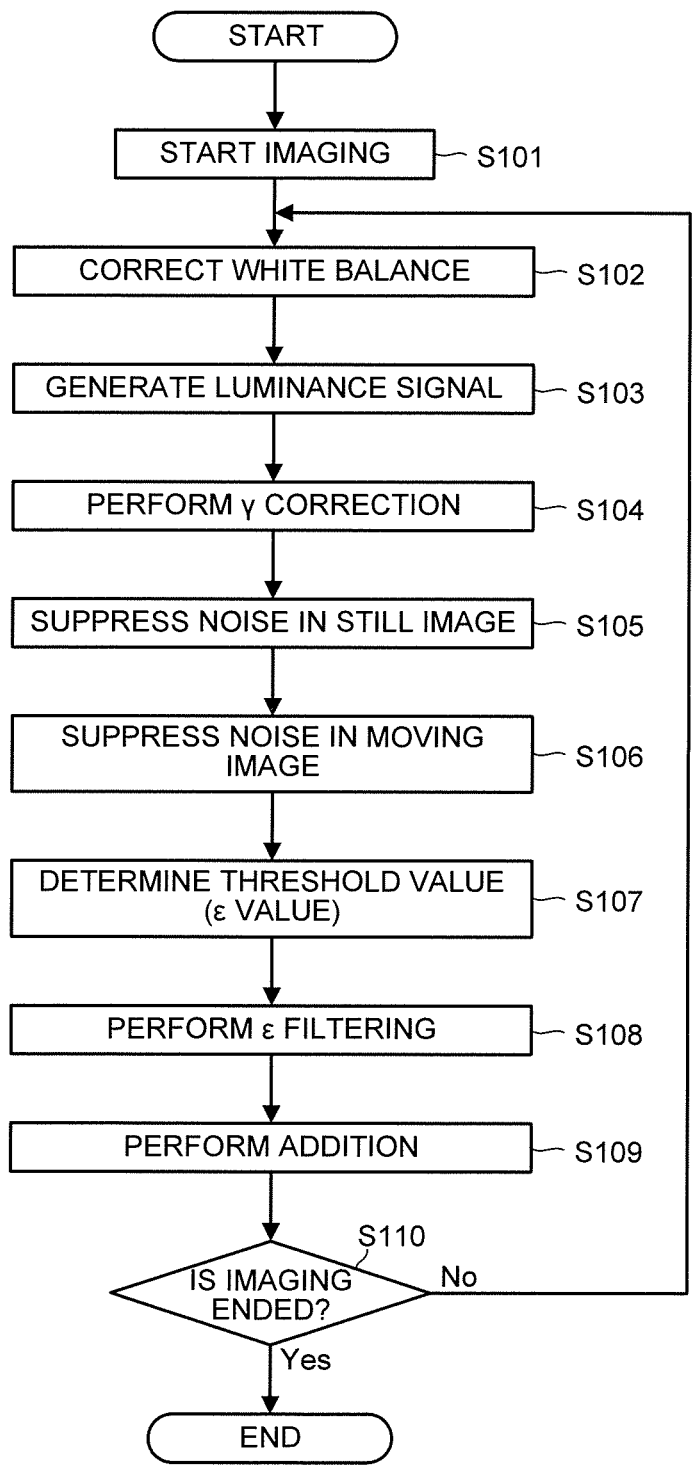
FIG. 10 is a flowchart showing an operation of the endoscopic apparatus according to the embodiment.

FIG. 10 is a flowchart showing an operation of the endoscopic apparatus according to the embodiment. Hereinafter, a correction operation of the endoscopic apparatus 1 will be described with reference to FIG. 10.

When imaging is started, an image signal is output from the image sensor 20a (Step S101). The white balance circuits 101a to 101c of the image signal processing unit 33a adjust white balance of image signals of the respective R, G, and B channels (Step S102).

The luminance signal generation circuit 104 generates a luminance signal Y on the basis of the RGB signals, the white balance of which have been adjusted (Step S103). The γ correction circuit 105 gamma-corrects the luminance signal Y (Step S104).

The noise reduction unit 203 of the three-dimensional noise reduction circuit 106 calculates an absolute value of a difference signal that is input from the γ correction circuit 105. The noise reduction unit 203 performs correction to reduce a mixing ratio with respect to the difference signal output from the γ correction circuit 105 in accordance with the magnitude of the calculated absolute value, to thereby suppress noise in the still image (Step S105).

The noise canceller unit 204 of the three-dimensional noise reduction circuit 106 calculates an absolute value of the difference signal that is input from the γ correction circuit 105. The noise canceller unit 204 corrects the difference signal output from the γ correction circuit 105 in accordance with the calculated absolute value, to thereby suppress noise caused in the moving image (Step S106).

The DTL control unit 205 calculates an absolute value V of the difference signal that is input from the γ correction circuit 105. The DTL control unit 205 determines, in accordance with a magnitude of the calculated absolute value V, an $\epsilon$ value (threshold value) of the first filter unit 301 and the second filter unit 302 included in the DTL unit 107 (Step S107).

The DTL unit 107 uses the $\epsilon$ value output from the DTL control unit 205 to perform filtering along the horizontal direction and the vertical direction (Step S108). The adders 103a to 103c add the signals output from the DTL unit 107 to the image signals of the respective R, G, and B channels (Step S109). The endoscopic apparatus 1 repeats the processing described above until the imaging is ended (Step S110).

As described above, the endoscopic apparatus 1 units relevant pixels into the three areas (X to Z) of the area X (still image area), the area Y (mixing area), and the area Z (moving image area), based on an absolute value V of a difference signal, and changes an $\epsilon$ value (threshold value) of the first filter unit 301 and the second filter unit 302 into an optimum value in accordance with the units. Therefore, noise in a portion of movement can be effectively reduced from an image signal.

Further, since the endoscopic apparatus 1 includes the H/V LPF 205a for removing a high-frequency component (noise) in a horizontal direction and a vertical direction, noise can be removed in both the horizontal direction and the vertical direction. Therefore, a movement of an image due to a difference signal can be accurately detected. In addition, since the maximum value of the $\epsilon$ value (threshold value) in the first filter unit 301 and the second filter unit 302 is set to a noise level, an image signal can be prevented from being excessively corrected (over-correction).

Furthermore, since a CMOS image sensor is adopted as an image sensor, a plurality of voltages are unnecessary and an operating voltage is low. Therefore, a power source to generate several voltages is unnecessary, with the result that manufacturing costs and a power consumption of the imaging apparatus can be suppressed. In addition, since devices of the CMOS image sensor can be made denser than those of a CCD image sensor, the endoscopic apparatus 1 can be further downsized.

Other Embodiments

While certain embodiments have been described, these embodiments have been presented by way of example only, and are not intended to limit the scope of the inventions. Indeed, the novel embodiments described herein may be embodied in a variety of other forms; furthermore, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image signal correction apparatus, comprising:
a frame memory that holds input luminance signals corresponding to a predetermined number of frames;
a difference calculation device that calculates a difference signal between an input luminance signal and each of the luminance signals held in the frame memory;
a controller that changes a first threshold value in accordance with a value of the difference signal calculated by the difference calculation device; and
a filter that passes a luminance signal having a value larger than the first threshold value and to perform filtering processing of a luminance signal having a value equal to or smaller than the first threshold value,
wherein the controller
(i) sets the first threshold value to zero in a case where the value of the difference signal is smaller than a second threshold value,
(ii) increases the first threshold value in accordance with the value of the difference signal in a case where the value of the difference signal is equal to or larger than the second threshold value and smaller than a third threshold value being larger than the second threshold value, and
(iii) sets the first threshold value to be constant when the value of the difference signal is equal to or larger than the third threshold value.

2. The apparatus according to claim 1,
wherein a relationship between the value of the difference signal and the first threshold value of the filter in the case where the value of the difference signal is equal to or larger than the second threshold value and smaller than the third threshold value is represented by a trigonometric function $$\epsilon(V) = N \cos\{\pi \times (V - TH2)/(2(TH1 - TH2))\},$$

where
"TH1" is the first threshold value,
"TH2" is the second threshold value,
"N" is a noise level, and
"V" is an absolute value of the difference signal.

3. The apparatus according to claim 2, wherein the difference calculation device comprises an adder.

4. The apparatus according to claim 2, wherein the controller comprises a detail (DTL) control device.

5. The apparatus according to claim 4, wherein the DTL control device comprises a horizontal/vertical (H/V) filter to remove noise of a horizontal component and a vertical component of the difference signal, and the controller changes the first threshold value of the filter in accordance with the value of the difference signal from which noise has been removed by the H/V filter.

6. The apparatus according to claim 1,
wherein the first threshold value of the filter in the case where the value of the difference signal is equal to or larger than the third threshold value is a noise level.

7. The apparatus according to claim 1, further comprising a horizontal/vertical (H/V) filter to remove noise of a horizontal component and a vertical component of the difference signal,
wherein the controller changes the first threshold value of the filter in accordance with the value of the difference signal from which noise has been removed by the H/V filter.

8. The apparatus according to claim 1, wherein the difference calculation device comprises an adder.

9. The apparatus according to claim 1, wherein the controller comprises a detail (DTL) control device.

10. The apparatus according to claim 9, wherein the DTL control device comprises a horizontal/vertical (H/V) filter to remove noise of a horizontal component and a vertical component of the difference signal, and the controller changes the first threshold value of the filter in accordance with the value of the difference signal from which noise has been removed by the H/V filter.

* * * * *